United States Patent [19]

Bommarito

[11] Patent Number: 4,575,946
[45] Date of Patent: Mar. 18, 1986

[54] OPHTHALMIC GUIDE FOR MULTI-FOCAL SPECTACLES

[76] Inventor: Paul F. Bommarito, 10684 Martinwood Way, Cupertino, Calif. 95014

[21] Appl. No.: 642,052

[22] Filed: Aug. 17, 1984

Related U.S. Application Data

[63] Continuation-in-part of Ser. No. 534,491, Sep. 3, 1983, abandoned.

[51] Int. Cl.⁴ ............................................. A61B 3/10
[52] U.S. Cl. .................................................... 33/200
[58] Field of Search ......................... 33/200; 351/204; 116/240

[56] References Cited

U.S. PATENT DOCUMENTS

| | | | |
|---|---|---|---|
| 1,621,352 | 3/1927 | Currier | 33/200 |
| 1,804,749 | 5/1931 | Desmond | 33/200 |
| 2,884,832 | 5/1959 | Engelmann | 351/204 |
| 3,987,554 | 10/1976 | Pastore | 33/200 |
| 4,024,831 | 5/1977 | Sperling | 116/240 X |

Primary Examiner—Harry N. Haroian
Attorney, Agent, or Firm—Thomas Schneck

[57] ABSTRACT

A measuring device for prescribing special multi-focal spectacles featuring transparent members which overlay ophthalmic lenses. Each member has at least one horizontal stripe which is optically distinct from the remainder of the member, such as by having different transmissivity to light or by having opaque edges. The stripe has a lengthwise dimension which spans a lens fitting into the frame of the user and a vertical width dimension corresponding to the apparent dimension of a video display terminal seen at a terminal viewing distance. The members may be moved up and down with respect to spectacles until the image of the terminal is blocked or otherwise marked by the stripe. An ophthalmic practitioner may then measure the location of a stripe edge relative to the top or bottom of a lens or spectacle socket, thereby locating a terminal viewing power zone.

12 Claims, 7 Drawing Figures

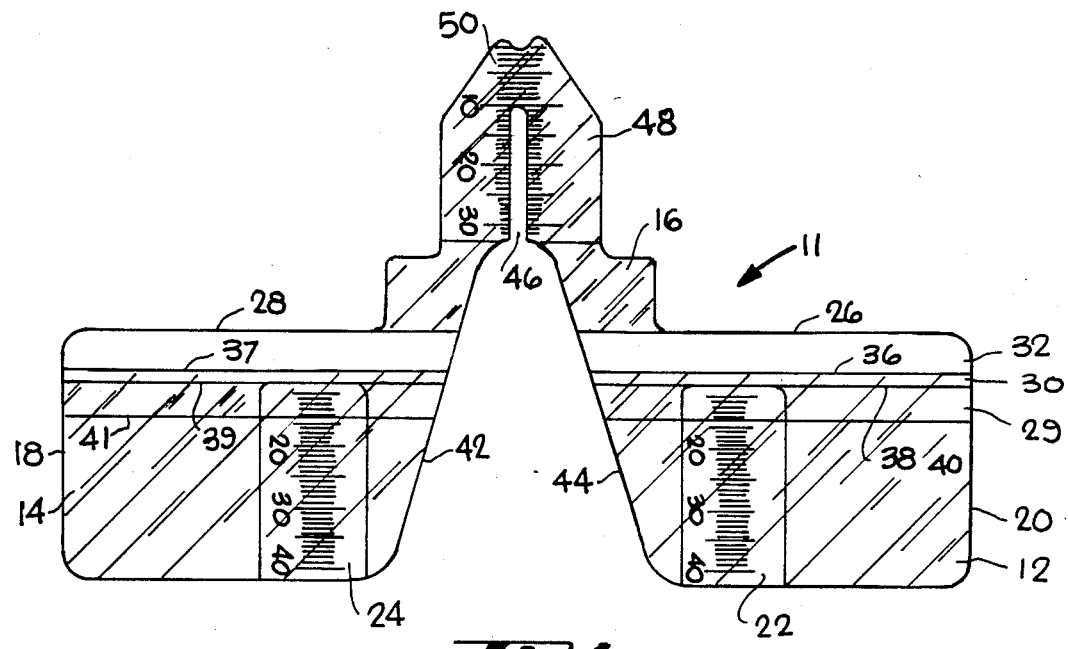
Fig. 1
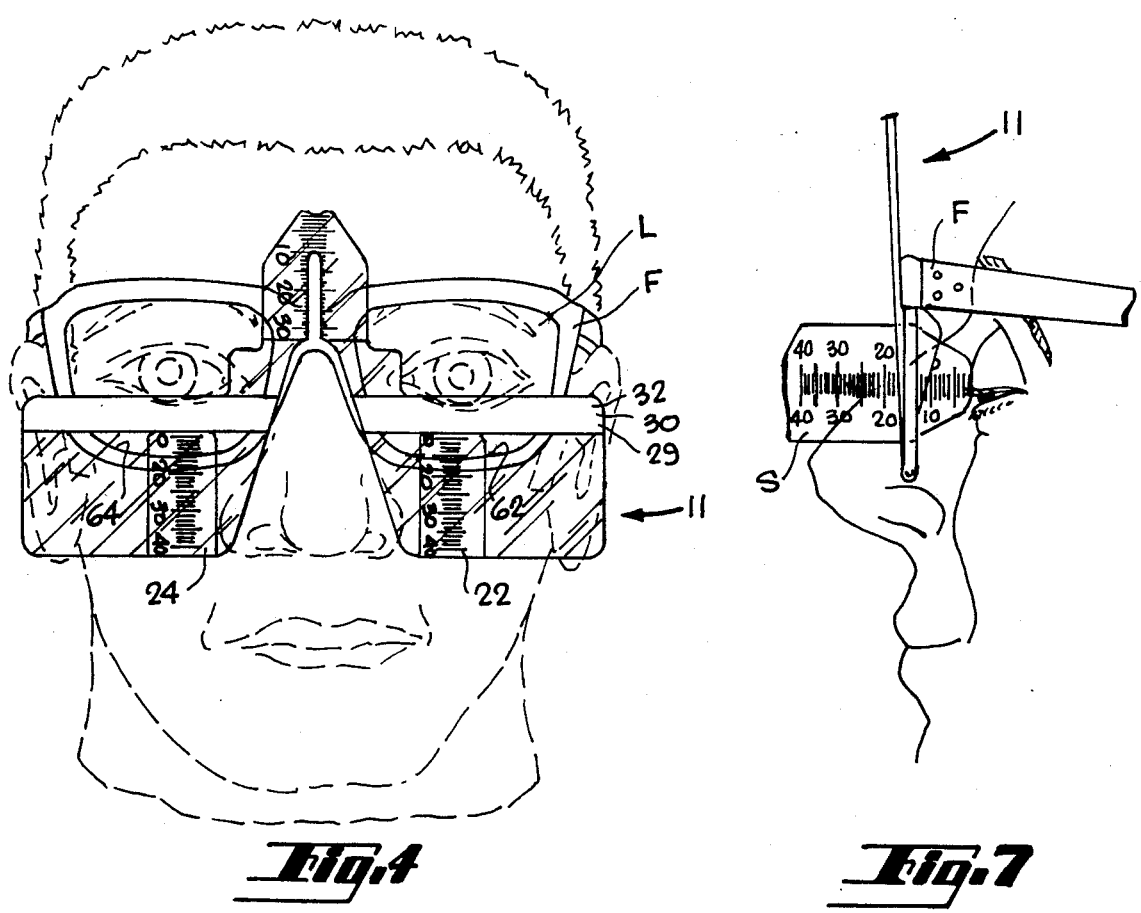
Fig. 4
Fig. 7

OPHTHALMIC GUIDE FOR MULTI-FOCAL SPECTACLES

This is a continuation-in-part of application Ser. No. 534,491 filed Sept. 3, 1983, now abandoned.

TECHNICAL FIELD

The invention relates to measuring instruments and more particularly to a device for prescribing multifocal spectacles where one of the focal powers is selected for viewing a video display terminal.

BACKGROUND ART

Devices for measuring the segment height of a bifocal line are known. The segment height is a distance from the bottom of a spectacle lens or socket to a dividing line between a first power of a lens, say for reading, separating a second power region, say for distance viewing. The location of the line is important for the comfort of a user of spectacles. If the line is too high, a user will be aware of the two power zones while viewing objects at a distance. If the line is too low, there will be an insufficient zone for observing objects using the lower lens region. Ophthalmic practitioners usually decide on a height on a lens where the segment line is desired. This distance is recorded and sent to a lens maker. A scale for use in this measurement is shown in U.S. Pat. No. 3,987,554 to Pastore.

In recent years, with the proliferation of computers and video display terminals, there has arisen a need for special multifocal lenses. Such lenses have three separate powers, typically including a first power for reading, a second power for viewing a computer screen or video terminal and a third power for distance viewing. One of the problems associated with such multifocal lenses is in locating and sizing the various power zones, particularly the second power zone. It is known that, in order to minimize distortion, the three power zones should be located with the intermediate power zone between higher and lower power zones. For example, it is known that a suitable arrangement would be distance viewing zone, intermediate power zone, reading zone, respectively, from top to bottom.

An object of the invention was to determine the location and size of a second power zone in a multi-focal lens, especially a power zone used for viewing a video display terminal.

SUMMARY OF THE INVENTION

The above object has been achieved with a generally transparent fixture which may be disposed over an ophthalmic lens and usually a portion of a frame supporting the lens as well. The fixture has a horizontal stripe with a lengthwise dimension spanning the lens and a vertical width dimension corresponding to the apparent dimension of a video display terminal seen at a terminal viewing distance such that the image of the terminal is blocked by the stripe if it is opaque. If the stripe is transparent, but has marked edges, the terminal can be seen, but its position falls between the two edges where a different power zone will be located. The lower edge forms a lower boundary for the zone which can be measured by a rule or the like.

Since viewers hold their heads at different distances from terminals and since the terminals themselves are of different size, it is useful to provide a plurality of stripes so that a viewer can see a terminal through one or more stripes. The combined vertical widthwise dimensions of the stripes needed to block out the image of the terminal represents the vertical width dimension of a power zone in a multifocal lens for viewing the terminal.

BRIEF DESCRIPTION OF THE DRAWINGS

FIG. 1 is a front view of a guide for prescribing multifocal spectacles in accord with the present invention.

FIG. 4 is a view of the prescribing guide of FIG. 1 shown in use over spectacle frames of a user.

FIG. 7 is a side operational view for a pupillary distance measurement using an ancillary feature of the present invention.

BEST MODE FOR CARRYING OUT THE INVENTION

Figure 3:
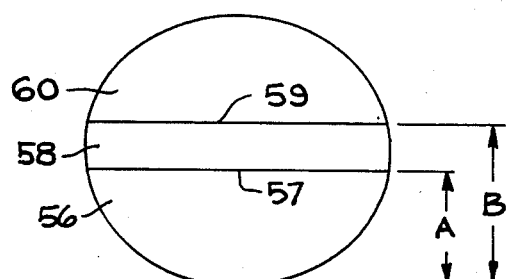
FIG. 3 is a plan view of a multifocal lens.

With reference to FIG. 1, an ophthalmic prescribing guide 11 is shown having a first side member 12, a second side member 14 and a bridge piece 16 joining the first and second side members. Each side member is somewhat larger than the socket of an average spectacle frame. The average vertical width of one of the side members at the midpoint in its height is approximately 6 cm and the average height in the center of a side member is approximately 4 cm. The overall length of the device from edge 18 to edge 20 is approximately 15.3 cm, although this distance is not critical. The edge-to-edge distance is also termed the hinge-to-hinge distance, by analogy to spectacle hinges normally located in the temple region of spectacle frames. The guide 11 may be considered to have a lengthwise axis which spans spectacle frames between edges 18 and 20, i.e. in the hinge-to-hinge direction. The actual hinge-to-hinge distance of spectacle frames should be slightly less than the edge-to-edge distance of the guide 11.

Each side member is transparent, being preferably made of clear plastic approximately 1 mm thick. Each side member carries a scale. The first side member 12 has a scale 22 while the second side member 14 has a scale 24, both of the scales being graduated in millimeters. The purpose of each of the scales is to judge segment height with respect to the bottom of a spectacle socket or lens. The zero of each scale lies along upper edge 26 for first side member 12 and along upper edge 28 for second side member 14.

In accord with the present invention, stripes are defined parallel to the lengthwise axis of the guide. The vertical width of each stripe is perpendicular to the length, and a single stripe, or a combination of stripes whose vertical widths are added together, is intended to have a vertical width corresponding to the apparent dimension of a video display terminal seen at a distance. That distance is the normal terminal viewing distance which is usually more than one foot away, but usually less than 3.5 feet away. A terminal user usually has a preferred viewing distance at which the apparent image of the terminal may be localized within a stripe or combination of stripes.

The first or top stripe 32 has a vertical width which might encompass the image of a terminal between upper edge 26 and first intermediate edge 36. The distance between these two edges is preferably about 7 mm. For a slightly expanded blocking zone a thin second stripe, defined between first intermediate edge 36 and second intermediate edge 38 is added. The distance between the two intermediate edges is approximately 3 mm. This will take into account slight variances in viewing distance or dimensions of the video display terminal whose image is to be blocked. For still further variances in the apparent dimension of the image or in the distance between the image and the viewer, a third stripe is defined between the second intermediate edge 38 and the lower edge 40. This third stripe is approximately 4 mm. parallel and adjacent to the other two stripes so that vertical widths of the three stripes can be combined additively, if needed.

A second side member has stripes defined between upper edge 28 and first intermediate edge 37; between first intermediate edge 37 and second intermediate edge 39 and between second intermediate edge 39 and the lower edge 41. These three stripes correspond in vertical width dimension to the three stripes defined in the first side member 12 and have similar lengths. The three stripes in each side member may be transparent, but edges should be marked such as by opaque lines so that a viewer can observe when an image is viewed through one or more stripes. To assist the viewer, the stripes may be tinted so that the opacity of the stripes differs from the opacity of the remainder of the side members. For example, the side members are typically clear and the stripes may be tinted red, by application of red filter material over the transparent side members. The stripe edges are still opaque so that each stripe may be defined. Also, each stripe may have a different tint for even greater definition, or, one of the stripes, such as the lower stripe, may be opaque. Alternatively, all stripes may be opaque with light transmissive edges.

The two side members have symmetric edges 42 and 44, intended to provide clearance for the bridge of the nose. Accordingly, each of the sloped edges 42 and 44 makes an angle of approximately 25° to the vertical. This angle could be a few degrees greater or smaller. The apex 46 of the two sloped regions is well above the colinear upper edges 26 and 28, approximately 1.5 cm above. This provision is made so that the guide of the present invention can slide along the bridge of the nose, moving the horizontal stripes vertically to intercept the optical axis between a user's pupils and the image of a video display terminal. Tab 48 has a scale 50 which can serve for another measurement, described below.

Figure 2:
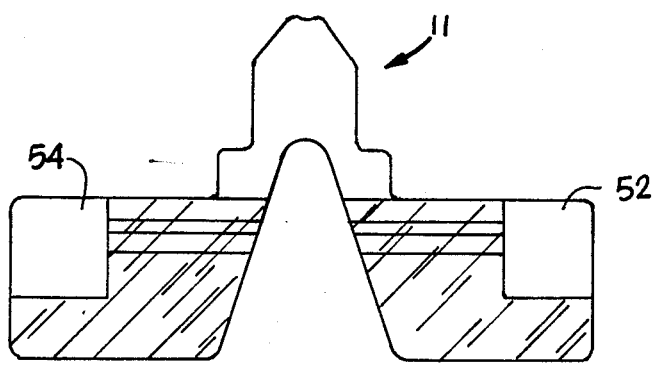
FIG. 2 is a backside view of the prescribing guide of FIG. 1.

With reference to FIG. 2, the backside of the guide 11 may be seen to have a pair of pads 52 and 54, one in each corner of a side member. Each pad is a very thin adhesive member such that the guide of the present invention may be adhered to spectacle frames if desired. If not desired, the adhesive pads 52 and 54 may be covered with thin strong paper so that the backside of the adhesive, i.e. the side facing a user, is protected. The opposite side of each pad has the same adhesive and is used to fasten the pad to the guide in the corner regions. When fitting persons wearing very small frames, it may be desirable to relocate the pads inwardly so that the pads can make contact with lenses or spectacle frames themselves.

FIG. 3 shows an ideal ophthalmic lens to be fitted on a video display terminal user having a need for a multifocal lens. Lower zone 56 is of a first power, intended for reading. This power might be plus 2 diopters. Intermediate zone 58 is of a second power, intended for viewing a video display terminal. This power might be plus 1 diopter and have an overall vertical width which is determined by the stripes previously described. Besides the vertical width of the intermediate zone 58, the instrument of the present invention locates this intermediate zone relative to the bottom of the lens or to a frame holding the lens. The distances, A and B on FIG. 3, are measured by means of scales 22 and 24 on FIG. 1. Use of the instrument of the present invention will be described below with reference to FIGS. 4 and 6. Upper power zone 60 is of a third power, intended for distance viewing. The segment height boundary lines 57 and 59, defined by the measured distances, A and B may be either abrupt transition lines, or may be gradually blended in the fashion known to progressive power lensmakers. In progressive power lenses, the lines between power zones are not as readily apparent as in traditional multifocal lenses. While the transition zone is not apparent, there is usually a slight amount of distortion in the transition between power zones in progressive power lenses. To hide the distortion, lensmakers sometimes attempt to relocate transition zones toward the opposite edges of the lens. This can sometimes be done by making power zone 58 a curved or irregular zone, rather than the straight band shown in FIG. 3. The segment height measured with the guide of this invention would be mathematically transformed, if necessary, for progressive power lens designs.

In FIG. 4, the guide 11 is placed on the nose of a user and slid up and down the nose until one or more of the stripes 32, 30 or 29 block the image of a video display terminal in front of the user. At that point, the number of bands blocking the images recorded and the distance from the lower boundary of such stripes is measured relative to the bottom edges 62 and 64 of lens sockets in frames F, holding the lens L, using scales 22 and 24. Since the vertical width of the stripes is known, the vertical width of the intermediate zone is readily known, as is its location relative to the bottom of a lens or frame.

Figure 5:
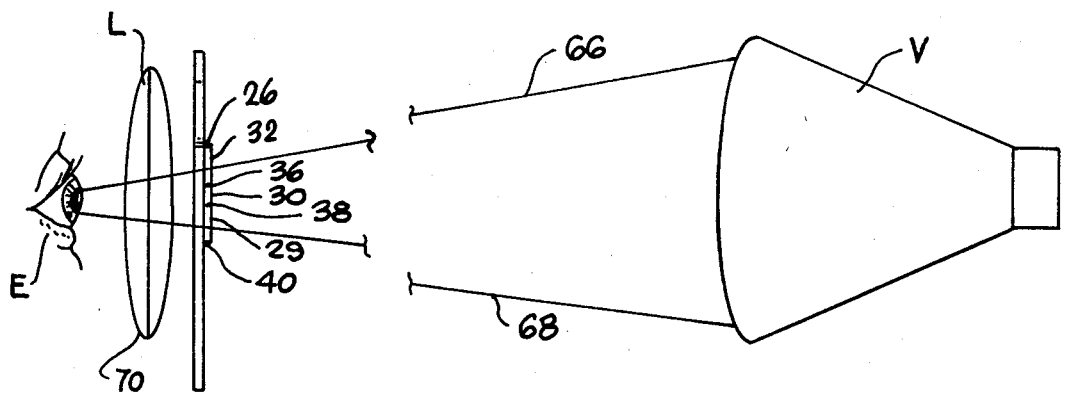
FIG. 5 is a side plan view of the manner of use of the prescribing guide of the present invention.

Use of the present invention is further illustrated in FIG. 5 wherein the eye E of a user is looking through lens L at video display terminal V. The guide of the present invention has the three stripes 32, 30 and 29 defined between edges 26, 36, 38 and 40 respectively. The video display terminal V has a screen area which creates an image defined by converging rays 66 and 68. These converging rays fall on stripes 32 and 29. Accordingly, the full vertical width of the stripes would be used to define the central power zone in a multifocal lens. In the previously given example, such an intermediate zone would be approximately 14 mm. wide since it would consist of the vertical width of upper stripe 32 or 7 mm., plus the vertical width of stripe 30 or 2 mm., plus the vertical width of lower stripe 29 or 5 mm. The distance from the bottom of lens L, 70, to the lower edge of the bottommost scale which was used, namely edge 40, is measured using the scale. This locates the segment height for the intermediate lens zone relative to the bottom of the lens.

Figure 6:
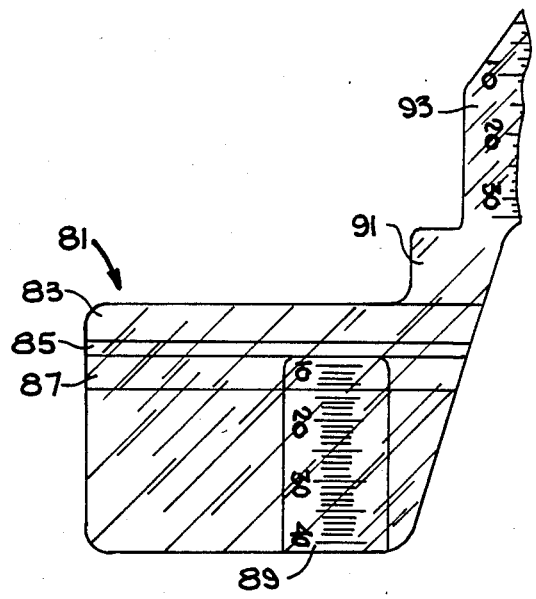
FIG. 6 is a front view of an alternate embodiment of the apparatus of FIG. 1 suitable for use with a single lens.

FIG. 6 shows a slightly modified version of the present invention wherein a guide 81 is a single side of the guide shown in FIG. 1. In this embodiment, the guide is used only over one eye and the assumption is made that the other eye is symmetrical. The fixture has three stripes, 83, 85 and 87, the stripes having edges extending across the fixture in directions parallel to the fixture lengthwise axis. As mentioned previously, the stripes have vertical widths which, when taken alone or combined might correspond to the apparent dimension of a video display terminal seen at a terminal viewing on distance. Once again, scale 89 is disposed on the fixture for measurement purposes. A tab 91 is provided so that the fixture may be held at a desired location adjacent the nose and in front of a spectacle frame of a user. The single lens version of the present invention may be made in such a way so that front and back sides are the same in this manner, the fixture could be placed over either left or right lens of a user.

In FIG. 1, apex 46 was shown having a slot immediately above the apex. Use of the slot is explained with reference to FIG. 7. In this figure, the guide 11 has been turned upside down and placed immediately in front of frames F, having no lenses in the lens socket. The slot may be used to accommodate a scale S to make a known measurement of distance of the eye from the lens socket. This measurement is necessary for calculating focal length. This measurement is well known to those skilled in the art and the scale and slot for accomplishing the same are not part of the present invention. These are merely described for a complete description of the preferred embodiment of the present invention.

I claim:

1. A guide for prescribing multifocal spectacles comprising,
   a transparent fixture to be placed over spectacles having a pair of zero power, planar, transparent members disposed in spectacle relationship, the fixture having a lengthwise axis spanning spectacle frames at least from hinge-to-hinge,
   a first stripe with defined edges disposed across portions of the fixture parallel to the lengthwise axis, the stipe having a vertical width corresponding to an apparent dimension of a video display terminal seen at a terminal viewing distance, and
   a second stripe with defined edges disposed parallel and adjacent to said first stripe, said second stripe having a width, when added to the vertical width of the first stripe, corresponding to an apparent dimension of a video display terminal seen at a distance.

2. The guide of claim 1 wherein said second stripe is translucent.

3. The guide of claim 1 wherein said second stripe is opaque.

4. The guide of claim 1 wherein the combined vertical width of said first and second stripes is in the range of 8 to 10 millimeters.

5. The guide of claim 1 wherein a third stripe with defined edges is disposed parallel and adjacent to said first and second stripes, said second stripe having a vertical width, when added to the vertical width of the first and second stripes, corresponding to an apparent dimension of a video display terminal seen at a distance.

6. The guide of claim 5 wherein said third stripe is translucent.

7. The guide of claim 5 wherein said third stripe is opaque.

8. The guide of claim 5 wherein the combined vertical width of said first, second and third stripes is in the range of 13 to 15 millimeters.

9. The guide of claim 1 having means for attachment to spectacle frames.

10. A guide for prescribing multifocal spectacles comprising,
    a transparent fixture disposable over an ophthalmic lens, said fixture having at least one horizontal stripe having a length-spanning-said lens and having-a vertical width dimension corresponding to the apparent dimension of a video display terminal seen at a terminal viewing distance, the stripe disposed in elevation over a prescribed first power zone and below a prescribed second power zone, defining a third power zone, and
    parallel, adjacent stripes having a combined vertical width corresponding to the apparent dimension of a video display terminal seen at a terminal viewing distance.

11. The guide of claim 10 having three parallel, adjacent stripes having a combined vertical width corresponding to the apparent dimension of a video display terminal seen at a terminal viewing distance.

12. The guide of claim 10 wherein a pair of said transparent fixtures are connected by a nose bridge member, spacing said fixtures to fit over a pair of ophthalmic lenses spaced at a distance commonly found in spectacles.

* * * * *

UNITED STATES PATENT AND TRADEMARK OFFICE
CERTIFICATE OF CORRECTION

PATENT NO. : 4,575,946
DATED : March 18, 1986
INVENTOR(S) : Paul F. Bommarito

It is certified that error appears in the above-identified patent and that said Letters Patent are hereby corrected as shown below:

Claim 1, line 10 "stipe" should read --stripe--.

Signed and Sealed this

Fifth Day of August 1986

[SEAL]

Attest:

DONALD J. QUIGG

Attesting Officer

Commissioner of Patents and Trademarks